(12) United States Patent
Huang (10) Patent No.: US 11,771,917 B2
(45) Date of Patent: Oct. 3, 2023

(54) METHOD AND APPARATUS FOR BRAIN FUNCTION ENHANCEMENT

(71) Applicant: Li-Da Huang, Austin, TX (US)

(72) Inventor: Li-Da Huang, Austin, TX (US)

( * ) Notice: Subject to any disclaimer, the term of this patent is extended or adjusted under 35 U.S.C. 154(b) by 337 days.

(21) Appl. No.: 17/037,329

(22) Filed: Sep. 29, 2020

(65) Prior Publication Data

US 2021/0023391 A1 Jan. 28, 2021

Related U.S. Application Data

(62) Division of application No. 15/861,504, filed on Jan. 3, 2018, now Pat. No. 10,821,298.

(60) Provisional application No. 62/441,829, filed on Jan. 3, 2017.

(51) Int. Cl.
*A61N 5/06* (2006.01)
*A61M 21/00* (2006.01)
*A61B 5/1455* (2006.01)
*A61B 5/055* (2006.01)
*A61B 5/369* (2021.01)

(52) U.S. Cl.
CPC ............ *A61N 5/0622* (2013.01); *A61M 21/00* (2013.01); *A61N 5/062* (2013.01); *A61B 5/055* (2013.01); *A61B 5/14553* (2013.01); *A61B 5/369* (2021.01); *A61M 2021/0005* (2013.01); *A61M 2021/0044* (2013.01); *A61M 2205/3375* (2013.01); *A61M 2205/50* (2013.01); *A61M 2230/10* (2013.01); *A61M 2230/205* (2013.01); *A61N 5/0618* (2013.01); *A61N 2005/0659* (2013.01)

(58) Field of Classification Search
CPC ...... A61N 5/06; A61N 5/0613; A61N 5/0618; A61N 5/0622; A61N 2005/0626; A61N 2005/0627; A61N 2005/0628; A61N 2005/0642; A61N 2005/0647; A61N 2005/065; A61N 2005/0651; A61N 2005/0652; A61N 2005/0658; A61N 2005/0659; A61N 2005/067; A61B 5/004; A61B 5/0042; A61B 5/055; A61B 5/1455; A61B 5/14553; A61M 2021/0005; A61M 2021/0044; A61M 2021/0055
USPC .............................. 607/88–91, 100, 108–110
See application file for complete search history.

(56) References Cited

U.S. PATENT DOCUMENTS

| | | | | |
|---|---|---|---|---|
| 2011/0144723 A1* | 6/2011 | Streeter | ................ | A61N 5/0618 607/88 |
| 2011/0295331 A1* | 12/2011 | Wells | .................. | A61N 5/0601 607/3 |
| 2014/0057232 A1* | 2/2014 | Wetmore | ............... | G09B 19/00 600/28 |

* cited by examiner

*Primary Examiner* — Ahmed M Farah
(74) *Attorney, Agent, or Firm* — Che-Yang Chen; Law Office of Michael Chen (57) ABSTRACT

In one aspect, a system for in vivo and transcranial stimulation of brain tissue of a subject may include at least one light source, a controller to control operation of the light source, a signal detecting unit and a processor configured to receive signals from the signal detecting unit, analyze the signals and generate a feedback signal to the controller to control the light source until optimal results are obtained. In one embodiment, the light source is a laser instrument and the wavelength can range from 800 to 1100 nm. In another embodiment, the irradiance of the laser instrument can range from 50 to 1000 mW/cm$^2$.

5 Claims, 9 Drawing Sheets

METHOD AND APPARATUS FOR BRAIN FUNCTION ENHANCEMENT

CROSS-REFERENCE TO RELATED APPLICATIONS

This application is a divisional application of application Ser. No. 15/861,504, filed on Jan. 3, 2018, which claims priority under 35 U.S.C. § 119 (e) to U.S. Provisional Patent Application Ser. No. 62/441,829, filed on Jan. 3, 2017, the entire contents of which are incorporated by reference.

FIELD OF THE INVENTION

The present invention relates to a method and apparatus for brain function enhancement, and more particularly to a photobiomodulation conducted with predetermined dosage, timing and location of the stimulation of the brain.

BACKGROUND OF THE INVENTION

Figure 1:
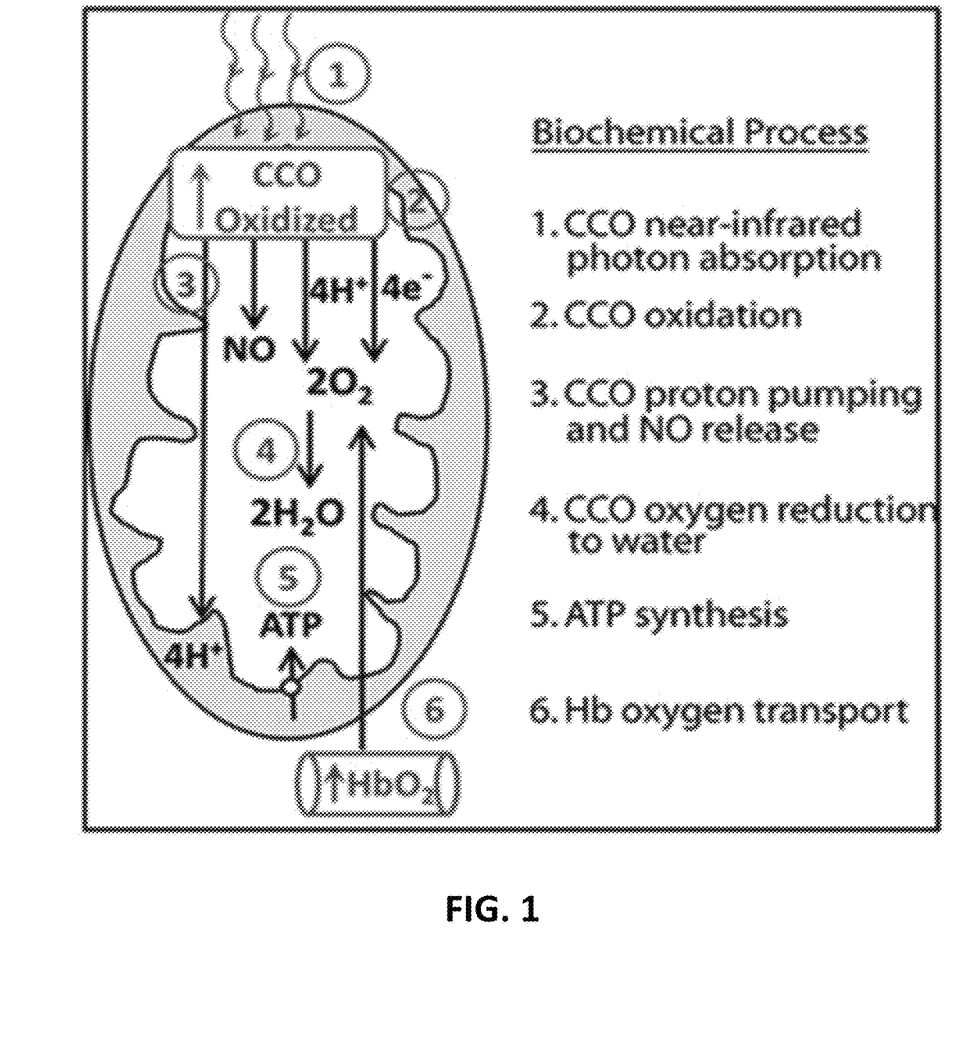
FIG. 1 is a schematic view of a mechanism of a mitochondrial respiratory enzyme cytochrome c oxidase (CCO) to convert high-energy photons into a source for ATP-based metabolic energy production in the brain.

Photobiomodulation involves the absorption of photons and the subsequent modulation of metabolic processes in cells, including neurons. For red to near-infrared light, the major intracellular molecule absorbing photons is cytochrome c oxidase (CCO), a mitochondrial respiratory enzyme that can be upregulated in vitro and in vivo. Upregulation of CCO serves to convert high-energy photons into a source for ATP-based metabolic energy production in the brain as shown in FIG. 1. Photobiomodulation of neural functions has been successful at 633-1070 nm wavelengths. For example, Naeser and collaborators pioneered using transcranial photobiomodulation with LED arrays of 633 and 870 nm in case studies showing improvement of cognitive functions in patients withmild traumatic brain injury. In addition, 1064 nm transcranial near-infrared laser stimulation (TILS) has been proven effective for increasing human cognitive and emotional functions in controlled studies using photobiomodulation aimed at the right prefrontal cortex. In particular, TILS of the human prefrontal cortex with a wavelength of 1064 nm increases the levels of oxidized cytochrome c oxidase, the conformation of the enzyme that has the highest activity, which leads to improved cerebral oxygenation. This photonicsbioenergetics in vivo mechanism is important for cognitive brain functions because nerve cells are critically dependent on oxidative energy metabolism.

It is hypothesized that TILS may also improve cognitive performance in middle-aged and older adults at risk for cognitive decline in general. This risk may be associated with aging-related subjective memory complaint, cardiovascular disease, or brain trauma. For example, cerebrovascular disease poses a severe threat to public health and is only expected to become more widespread as the worldwide population ages. Specifically, atherosclerosis of the carotid artery is a strong predictor of cognitive decline. The carotid artery intima-media thickness (IMT) is also recognized as a risk factor for brain damage in asymptomatic patients.

Middle-aged and older adults reporting memory complaint, showing early signs of carotid atherosclerosis (increased IMT values) or with a history of brain trauma, are prime candidates for early interventions aimed to minimize or prevent cognitive decline. One potential non-invasive intervention may be increasing cerebral oxygenation by upregulating mitochondrial respiration using TILS.

However, current TILS does not disclose a feedback control mechanism to generate an optimal dosage, timing and location of the light source to enhance brain stimulation. Therefore, there remains a need for a new and improved method and system for brain function enhancement to overcome the problems stated above.

SUMMARY OF THE INVENTION

It is an object of the present invention to provide a method and apparatus to enhance metabolism of a brain and improve its cognitive and memory functions.

It is another object of the present invention to provide a method and apparatus for brain function enhancement wherein a photobiomodulation is conducted with predetermined dosage, timing and location of the stimulation of the brain.

It is a further object of the present invention to provide a method and apparatus for brain function enhancement wherein a feedback loop control is implemented to achieve the optimal results of brain function enhancement.

In one aspect, a system for in vivo and transcranial stimulation of brain tissue of a subject may include at least one light source, a controller to control operation of the light source, a signal detecting unit; and a processor configured to receive signals from the signal detecting unit, analyze the signals and generate a feedback signal to the controller to control the light source, wherein the detected signal is processed through Fourier Transform (FT) with at least one predetermined time window, which is divided by the value of the detected signal transformed by FT and integrated for a predetermined bandwidth to generate a normalized FT signals to compare with one existing signals saved in a memory unit in the processor to determine and generate the feedback signal. In one embodiment, the processor can also be configured to extract feature points to feed into at least one machine learning algorithms to learn and identify brain status. It is noted that the feature points include, but no limited to peaks and valleys of the normalized FT signals, including the frequencies, amplitudes, bandwidth of the integration for normalization, the integration values, the time window to get the FT and the duration of the normalized FT spectrum.

In one embodiment, the light source is a laser instrument and the wavelength thereof can range from 800-1100 nm. In another embodiment, the irradiance of the laser instrument can range from 50-1000 mW/cm$^2$; and the laser can be directed at the right forehead, targeting the right prefrontal cortex, the area of the brain with the strongest relationship between carotid IMT and working memory performance. The laser aperture can be adjusted to a desired spot size from the diameter from 1 to 45 mm. About 1.2% of the 1064 nm laser light with the energy intensity of 60 J/cm$^2$ passed through the subject's frontal skull, so a peak hormetic dose of 1.2 J/cm$^2$ can reach the cerebral cortex.

In a further embodiment, the detecting unit is configured to detect the brain activity through EEG signals, fMRI images, BOLD data, etc., and the detected data or signals are transmitted to the processor to analyze to determine whether the dosage, timing and location of the brain stimulation has to be adjusted, and the feedback loop control can be conducted for one or more times until the optimal results are obtained.

In another aspect, a method for in vivo and transcranial stimulation of brain tissue of a subject may include steps of providing at least one light source, placing the light source near the exterior of the head of the subject to stimulate the subject's brain tissue; detecting signals for before and after the brain stimulation; and analyzing detected signals and generating a feedback loop control to adjust dosage, timing and location of the light source based on the analyzed results, wherein the step of generating a feedback control signal includes steps of conducting Fourier Transform on detected signals in at least one predetermined time window for a predetermined bandwidth, integrating the Fourier transformed signals for the predetermined bandwidth, generating a normalized signal by dividing the integrated Fourier transformed signals with the Fourier transformed signals, and comparing the normalized signal with at least one existing signal to generate the feedback control signal.

DETAILED DESCRIPTION OF THE INVENTION

The detailed description set forth below is intended as a description of the presently exemplary device provided in accordance with aspects of the present invention and is not intended to represent the only forms in which the present invention may be prepared or utilized. It is to be understood, rather, that the same or equivalent functions and components may be accomplished by different embodiments that are also intended to be encompassed within the spirit and scope of the invention.

Unless defined otherwise, all technical and scientific terms used herein have the same meaning as commonly understood to one of ordinary skill in the art to which this invention belongs. Although any methods, devices and materials similar or equivalent to those described can be used in the practice or testing of the invention, the exemplary methods, devices and materials are now described.

All publications mentioned are incorporated by reference for the purpose of describing and disclosing, for example, the designs and methodologies that are described in the publications that might be used in connection with the presently described invention. The publications listed or discussed above, below and throughout the text are provided solely for their disclosure prior to the filing date of the present application. Nothing herein is to be construed as an admission that the inventors are not entitled to antedate such disclosure by virtue of prior invention.

As used in the description herein and throughout the claims that follow, the meaning of "a", "an", and "the" includes reference to the plural unless the context clearly dictates otherwise. Also, as used in the description herein and throughout the claims that follow, the terms "comprise or comprising", "include or including", "have or having", "contain or containing" and the like are to be understood to be open-ended, i.e., to mean including but not limited to. As used in the description herein and throughout the claims that follow, the meaning of "in" includes "in" and "on" unless the context clearly dictates otherwise.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the embodiments. As used herein, the term "and/or" includes any and all combinations of one or more of the associated listed items.

Figure 2:
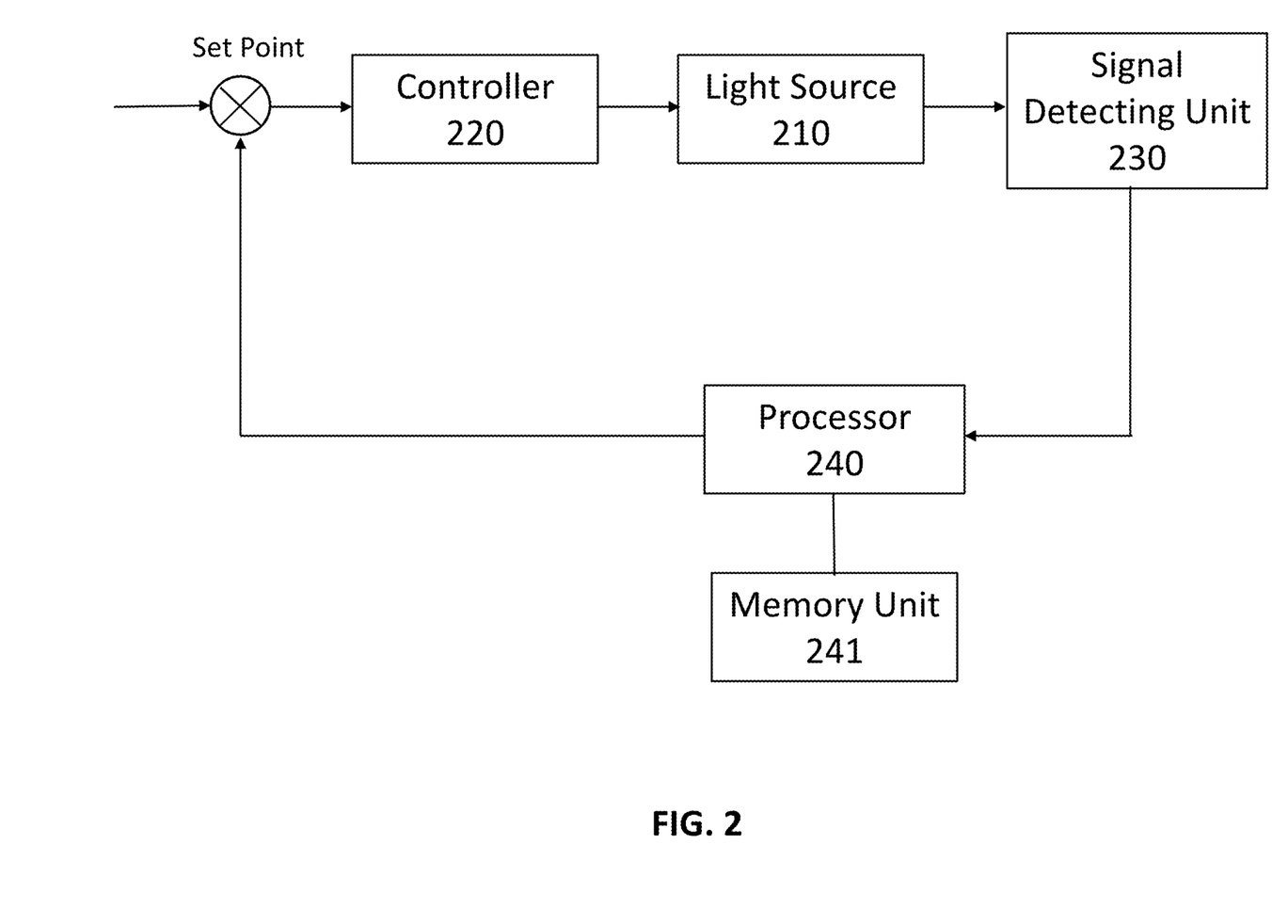
FIG. 2 is a schematic view of the feedback loop control of the system for in vivo and transcranial stimulation of brain tissue of a subject in the present invention.

In one aspect, as shown in FIG. 2, a system 200 for in vivo and transcranial stimulation of brain tissue of a subject may include at least one light source 210, a controller to control operation of the light source 220, a signal detecting unit 230 and a processor 240 configured to receive signals from the signal detecting unit 230, analyze the signals and generate a feedback signal to the controller 220 to control the light source 210, wherein the detected signal is processed through Fourier Transform (FT) with at least one predetermined time window, which is divided by the value of the detected signal transformed by FT and integrated for a predetermined bandwidth to generate a normalized FT signals to compare with one existing signals saved in a memory unit 241 in the processor 240 to determine and generate the feedback signal. In one embodiment, the processor 240 can also be configured to extract feature points to feed into at least one machine learning algorithms to learn and identify brain status. It is noted that the feature points include, but no limited to peaks and valleys of the normalized FT signals, including the frequencies, amplitudes, bandwidth of the integration for normalization, the integration values, the time window to get the FT and the duration of the normalized FT spectrum.

As stated above, the present invention is configured to conduct a photobiomodulation with predetermined dosage, timing and location of the stimulation of the brain. More specifically, the present invention is configured to use infrared photons to oxidize cytochrome c oxidase (CCO) to enable cerebral oxygenation to eventually achieve the goal of cognitive enhancement. In one embodiment, the light source 210 is a laser instrument and the wavelength thereof can range from 800-1100 nm. The transcranial stimulation in the present invention can be a transcranial near-infrared laser stimulation (TILS) and can be administered once a week for 5 weeks, following the same stimulation procedure as in an approved IRB protocol and as reported in Barrett and Gonzalez-Lima. More specifically, administration of TILS in the present invention including applying near-infrared light of a specific wavelength (1064 nm) using a well-collimated laser diode (HD laser, Cell Gen Therapeutics, Dallas, Tex.), and the laser beam was circular, with a uniform intensity profile (flat-top) and an area of 13.6 cm$^2$. In addition, the laser has a homogeneous beam power distribution achieved by an optical lens system mounted on the handpiece as measured at 1064 nm by an optical power meter (Model 1916-C) and photodiode detectors (Model 918D/918L) manufactured by Newport (Newport Corp., Irvine, Calif., USA) that systematically measured each spot of the beam area with independent and overlapping 0.44 to 1-cm$^2$ detectors.

Regarding the laser dose, in one embodiment, the laser wave was continuous (CW), and the power output used was 3.4 W for all treated groups. In another embodiment, the laser wave can be pulsed. The irradiance (power density) used for all treated groups was 250 mW/cm$^2$ (3400 mW/13.6 cm$^2$=250 mW/cm$^2$) and the laser dose can be adjusted by the controller 220 from 50 to 1000 mW/cm$^2$. For cognitive and fMRI studies, the laser exposure time was 240 second per site for two forehead sites, and thus, the fluence dose (energy density) used was 60 J/cm$^2$ (0.25 W/cm$^2$×240 second=60 J/cm$^2$) per site. Therefore, for the cognitive and fMRI studies, the forehead cumulative fluence dose per session was 220 J/cm$^2$ (60 J/cm$^2$×2 forehead sites=220 J/cm$^2$). It is noted that these are the same parameters that previously showed psychologically beneficial effects.

Figure 3:
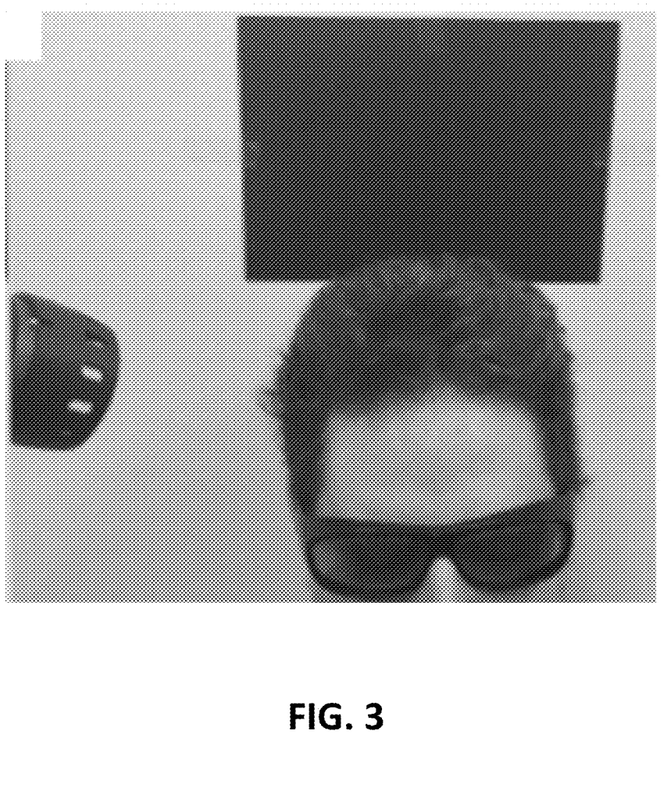
FIG. 3 illustrates a schematic view of conducting transcranial near-infrared laser stimulation on a subject in the present invention.

In the present invention, the laser can be directed at the right forehead as shown in FIG. 3, targeting the right prefrontal cortex, the area of the brain with the strongest relationship between carotid IMT and working memory performance. The forehead stimulation location covered a 4.2-cm diameter medial site (site 1) and a 4.2-cm diameter lateral site (site 2) with respect to the right frontal pole (FP2 point in the standard 10-20 EEG placement system). The laser stimulation was alternated every minute between these sites to prevent heating of the skin and to fractionate the dose for a total of 4 minutes per site (3.4 W×240 s=816 J/site). In one embodiment, the total treatment duration can be lasted for 8 minutes for each session and repeated weekly for 5 weeks.

It is noted that for the EEG study, TILS irradiance was also 250 mW/cm$^2$, but radiant exposure time was 55 seconds per 1-minute cycle, so that during the 5-second TILS-off period, the EEG recordings would be completely free from any stimulation-induced artifact. With 55 seconds of laser exposure per cycle, the laser fluence dose per cycle was 0.25 W/cm$^2$×55 s=13.75 J/cm$^2$. The laser energy delivered per cycle was 3.4 W×55 s=187 J. There were ten 55-second cycles in total of TILS during each EEG recording session. Only a single forehead site centered at FP2 was stimulated. Therefore, for the EEG study, the cumulative fluence dose per session was 137.5 J/cm$^2$ (0.25 W/cm$^2$×550 s=137.5 J/cm$^2$).

It has been verified previously that these TILS parameters effectively enhance cerebral oxygenation and cytochrome c oxidase levels in humans. At the parameters described, the power density at this setting is one quarter of the skin maximum permissible exposure (MPE) of 1 W/cm2 (ANSI, American National Standard for Safety Use of Lasers, Z136.1, Laser Institute of America, Orlando, 2014). It is not deemed harmful to tissue, and it causes no detectable physical damage and negligible heat. The laser's power output was automatically calibrated by an internal mechanism every time the user set a power level. TILS took place in a locked room in the Gonzalez-Lima lab that has been approved by the University of Texas at Austin Laser Safety Program for housing of the laser apparatus.

In one embodiment, the signal detecting unit 230 is configured to obtain ultrasound scan Images of the carotid artery. For example, the ultrasound scan Images can be obtained using a GE LOGIQ e Ultrasound System. More specifically, a longitudinal image (B mode) of the cephalic portion of the common carotid artery was acquired at 90° to the vessels, thus giving clear images of the near and far walls. Subsequently, ultrasound images can be analyzed by the processor 240. For example, ultrasound images can be analyzed by a computerized image analysis software (Vascular Research Tool Carotid Analyzer, Medical Imaging Applications, Coralville, Iowa). Carotid IMT is defined as the distance between the leading edge of the lumen-intima interface and the leading edge of the media-adventitia interface of the far wall.

In another embodiment, the signal detecting unit 230 can be configured to detect the subject's EEG signals after the subject is exposed to the light source 210 as stated above. In the present invention, standard EEG detecting methods are used to record scalp EEG signals using electrodes placed over the frontal, temporal, parietal, and occipital lobes of both hemispheres. Since the EEG alpha wave is more obvious than other wave frequencies when eyes are closed, the waves during eyes closed and open conditions are both recorded by the signal detecting unit 230. More specifically, the eyes were open for 5 seconds and closed for 55 seconds during each recording cycle (1-minute epoch). The motions of opening and closing the eyes provided clear EEG signals that served to mark each epoch in order to have consistent measurements. In each of six subjects who underwent EEG examinations, EEG was continuously recorded before, during, and after TILS in three successive periods: (1) 10 times of 55-second closed eyes, 5-second open eyes, without TILS; (2) 10 times of 55-second closed eyes with TILS, 5-second of open eyes; and (3) 10 times of 55-second closed eyes, 5-second open eyes, without TILS. The total EEG recording time was 30 min/subject.

In still another embodiment, the signal detecting unit 230 can be configured to obtain the subject's fMRI Imaging data which can be acquired during cognitive tests done at pre-TILS and post-TILS. For instance, anatomical scans of the entire brain were collected in the sagittal plane using a high-resolution ultrafast gradient echo 3D (MPRAGE) sequence (256×256 matrix, flip angle=7°, field of view (FOV)=24×24 cm$^2$, 1-mm slice thickness, 0 gap). Functional MRI was performed during completion of the two-back verbal working memory using a whole-brain echo-planar imaging sequence (TR=3000 ms, TE=30 ms, flip angle=90°, FOV=24×24 cm$^2$, 64×64 matrix, 42 axial slices, 3-mm slice thickness, 0.3-mm gap). During this task, participants are asked to decide if a letter appearing on a screen is the letter H (zero-back control condition) or the same as the letter that appeared one or two stimuli earlier (n-back working memory condition). Each letter is displayed for 500 ms with 2500 ms interstimulus interval during which the person can make a response using an MRI-compatible button box. All letters are consonants presented in random order, organized in alternating blocks of 12 (zero-back) or 15 (one-back and two-back) consonants. Of the letters, 33% are targets. Each of the two runs of the task consist of three alternating zero-back, one-back, and two back blocks. Mean accuracy and reaction time for correct trials are used as performance indicators. All EPI images were processed by the processor 240. For example, the EPI images can be analyzed with Analysis of Functional Neuro Images (AFNI) software. Each time series was spatially registered to the sixth volume of the session. The resulting information on displacement and rotation of each volume was later used to correct for head motion. Pre-processing steps also included temporal smoothing and spatial blurring using a 4.5-mm kernel. Averaged task-related activation, to be used as an outcome measure in subsequent analyses, was extracted from a set of a priori regions of interest (ROIs) where signal intensity changes have been shown to be significantly related to two-back performance in an independent sample, to avoid circularity.

In a further embodiment, the signal detecting unit 230 can be used to detect Blood-Oxygen-Level-Dependent (BOLD) data were during pre-TILS and post-TILS treatments for a number of subjects that are carefully selected so that they have varying levels of thickness of the carotid artery wall, as measured by ultrasound. It is noted that the blood oxygen level can also be detected by functional near-infrared spectroscopy (fNIRS). In still a further embodiment, the signal detecting unit 230 can be used to detect the concentration of oxidize cytochrome c oxidase (CCO) during pre-TILS and post-TILS treatments.

In still a further embodiment, the difference between pre-TILS and post-TILS treatment can be obtained through cognitive performance, which includes a sequence of events for the cognitive study as listed below: (1) Confirmation of subject screening with exclusionary/inclusionary criteria; (2) Medical questionnaire and informed consent document are filled out; (3) Ultrasound for carotid artery intima-media thickness (IMT) measurement (half hour); (4) Brief introduction to the psychomotor vigilance task (PVT) (1 min); (5) Baseline cognitive testing with PVT (5 min); (6) Brief introduction to the delayed match-to-sample task (DMS) (1 min); (7) Baseline cognitive testing with DMS (5 min); (8) First treatment with TILS (8 min); (9) Post-treatment cognitive testing with PVT (5 min); (10) Post-treatment cognitive testing with DMS (5 min). It is noted that for (11) to (14) below: each subsequent week for 4 additional weeks; session duration: 30 minutes: (11) Subjects answer the question, "Did you have any side effects from the treatment?" (12) Weekly continuing treatment with TILS (8 min); (13) Post-treatment cognitive testing with PVT (5 min); (14) Post-treatment cognitive testing with DMS (5 min); and 16. Contacted by email, subjects will answer the side-effects question a final time (one week after final TILS treatment session).

Cognitive performance was assessed using two tasks: the psychomotor vigilance task (PVT), a test of sustained attention, and the delayed match-to-sample memory task (DMS), a test of visual working memory. The prefrontal cortex region that the TILS targeted is involved in these cognitive tasks. The first testing session was a pre-treatment baseline evaluation (this was preceded by a brief 1-min-long introduction to both tasks; these data were not recorded). After the weekly TILS, participants repeated the PVT and DMS tasks for 5 weeks in total. We have previously demonstrated an improvement in performance on both the PVT and DMS tasks after a single TILS in healthy young adults, but we have not previously investigated the effects of repeated weekly TILS sessions.

The PVT is a reaction time test in which participants attend to a small fixation point at the center of a computer screen. At random intervals, a bright millisecond timer appears in the center of the screen. Participants are instructed to respond via button press as rapidly as possible upon detection of the counter stimulus; participant response stops the counter from updating. The final counter value corresponds to the participant's reaction time and is briefly displayed on-screen, thus providing feedback for that particular trial. If a participant makes a key press prior to the onset of the timer, the feedback "Too soon" is displayed on screen. Information about each trial's reaction time is stored for later analysis. The block of 40 PVT trials is approximately 5 minutes long; intertrial intervals are pseudo-randomly chosen without replacement from between 2 and 10 seconds; thus, the average intertrial interval is around 6 seconds.

The DMS also measures attention and reaction time but has a short-term memory component as well. Participants view a 6×6 grid of brightly colored yellow and red squares with a unique pattern. Then, with a key press, that stimulus disappears, and the screen is blank through a delay; then, two stimuli are presented on screen (a "match" and "non-match"). The participant indicates which stimulus is the correct match with a key press. Feedback (correct or incorrect) is briefly displayed onscreen before the next trial commences. Success/failure and reaction time across 30 trials are measured by the computer and stored for later analysis.

It is important to note that the present invention provides a feedback loop control to control the dosage, timing and location of the stimulation of the brain, as shown in FIG. 2. For example, an initial dosage of the light source 210, e.g. laser, can be provided to start the process of brain stimulation. The detecting unit 230 is configured to detect the brain activity through EEG signals, fMRI images, BOLD data, etc., and the detected data or signals are transmitted to the processor 240 to analyze to determine whether the dosage, timing and location of the brain stimulation has to be adjusted, and the feedback loop control can be conducted for one or more times until the optimal results are obtained.

Figure 4:
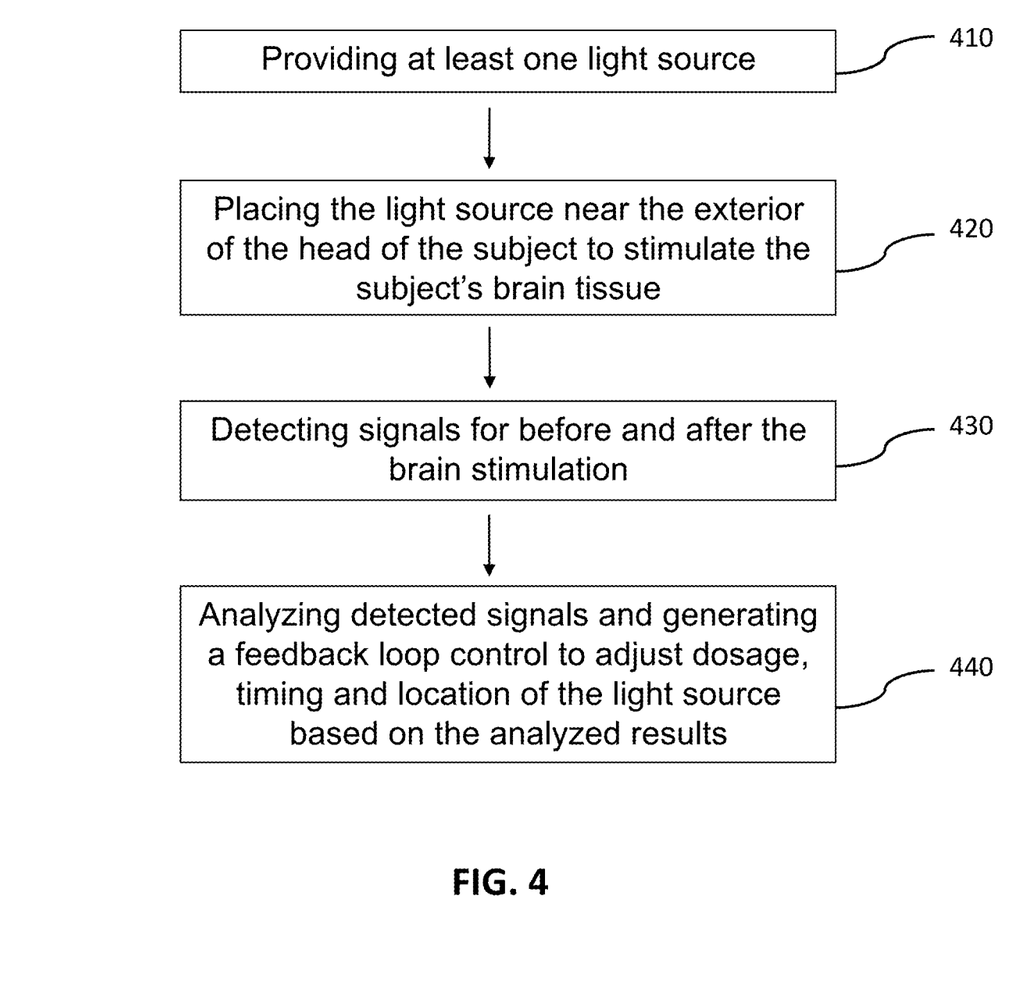
FIG. 4 illustrates a block diagram of a method for in vivo and transcranial stimulation of brain tissue of a subject in the present invention.

In another aspect, a method for in vivo and transcranial stimulation of brain tissue of a subject may include steps of providing at least one light source 410, placing the light source near the exterior of the head of the subject to stimulate the subject's brain tissue 420; detecting signals for before and after the brain stimulation 430; and analyzing detected signals and generating a feedback control signal to adjust dosage, timing and location of the light source based on the analyzed results 440, wherein the step of analyzing detected signals and generating a feedback control signal 440 includes steps of conducting Fourier Transform on detected signals in at least one predetermined time window for a predetermined bandwidth 441, integrating the Fourier transformed signals for the predetermined bandwidth 442, generating a normalized signal by dividing the integrated Fourier transformed signals with the Fourier transformed signals 443, and comparing the normalized signal with at least one existing signal to generate the feedback control signal 444.

In one embodiment, the step of analyzing detected signals and generating a feedback control signal 440 may further include a step of extracting feature points to feed into at least one machine learning algorithms to learn and identify brain status 450. It is noted that the feature points include, but no limited to peaks and valleys of the normalized FT signals, including the frequencies, amplitudes, bandwidth of the integration for normalization, the integration values, the time window to get the FT and the duration of the normalized FT spectrum.

In another embodiment, the light source in step 410 is a laser instrument wherein the wavelength thereof can range from 800 to 1100 nm and the irradiance of the laser instrument is 50 to 1000 $mW/cm^2$. In a further embodiment, in step 420, the laser can be directed at the right forehead, targeting the right prefrontal cortex, the area of the brain with the strongest relationship between carotid IMT and working memory performance. More specifically, the laser aperture can be adjusted to a desired spot size from the diameter from 1 to 45 mm. About 1.2% of the 1064 nm laser light with the energy intensity of 60 $J/cm^2$ passed through the subject's frontal skull, so a peak hormetic dose of 1.2 $J/cm^2$ can reach the cerebral cortex.

In still a further embodiment, the step of detecting signals for before and after the brain stimulation 430 may include the step of detecting the brain activity through EEG signals, fMRI images, BOLD data, etc., and step 440 is configured to receive and analyze the detected data or signals to determine whether the dosage, timing and location of the brain stimulation has to be adjusted, and the feedback loop control can be conducted for one or more times until the optimal results are obtained. The "Results" section below shows the effect of brain function enhancement after conducting photobiomodulation.

RESULTS

I. Cognitive Enhancement after TILS in Older Adults

Figure 5A:
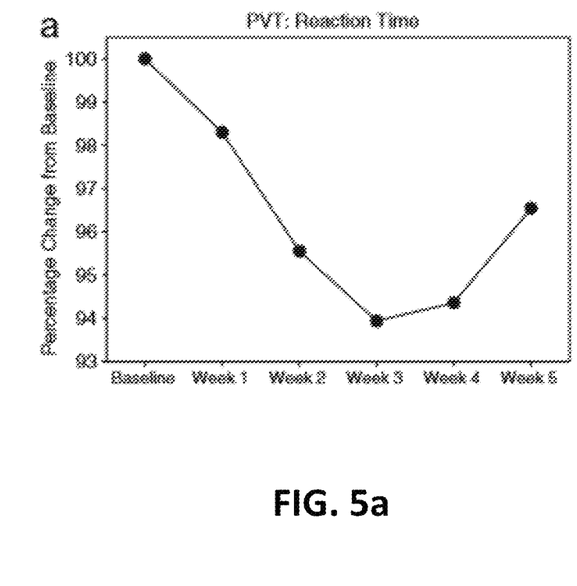
FIGS. 5a and 5b illustrates a normalized mean performance (n=12) on the psychomotor vigilance test (a PVT) and delayed match-to-sample test (b DMS) across 5 weeks of treatment. Reaction time and number of correct trials are expressed as the percentage change from performance at baseline. Subjects showed progressively faster responding in the PVT and progressively more accurate responses in the DMS, over weeks of laser treatment. The apparently weaker mean effects for week 5 were due to three subjects approaching ceiling performance and missing the last session.
Figure 5B:
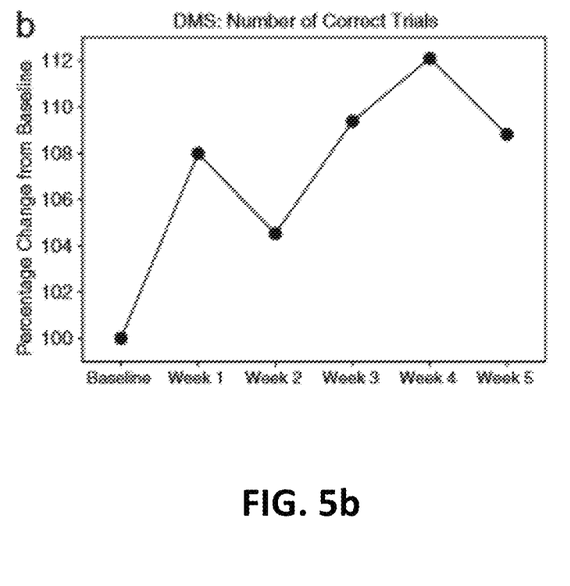

All participants in this older sample (ages 49 to 90 with a median age of 56) improved after repeated treatments in all cognitive measures as stated above. Reaction time (in ms) and number of lapses (trials in which the subject failed to respond within 500 ms of the stimulus) were recorded for the PVT; the number of correct responses was recorded for the DMS. The normalized data using percentage change from baseline demonstrated that all subjects improved over time after repeated treatments (FIGS. 5a and 5b). For a repeated measures ANOVA on the PVT data (FIG. 5a), using six data points (baseline+5 weeks of treatment), and using percentage change from baseline as the dependent variable, the effect of the within-subject variable (session) was significant: $F(5, 40)=2.7877$, $p<0.03$. Also, a repeated measures ANOVA on the DMS data (FIG. 5b), using six data points (baseline+5 weeks of treatment), using percentage change from baseline as the dependent variable, showed that the effect of the within-subject variable (session) was significant: $F(5, 40)=3.5799$, $p<0.01$.

Figure 6:
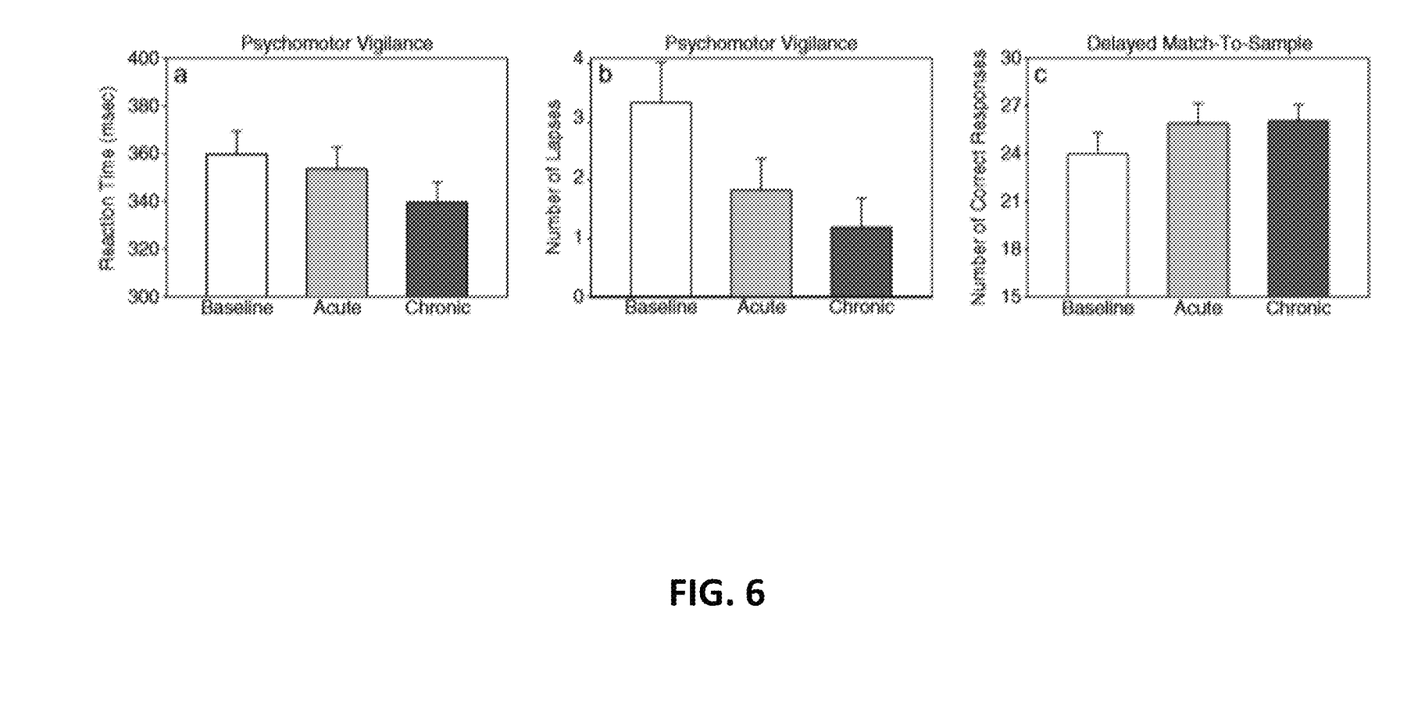
FIG. 6 illustrates a cognitive effects of 1064-nm laser treatment on attention and memory in older adults with subjective memory complaint (n=12) in the present invention.

FIG. 6 illustrates mean cognitive scores for baseline vs. acute (after a single session at week 1) pair-wise comparisons, where paired t tests indicated significant improvements for PVT lapses ($p<0.001$), but not for PVT reaction time ($p=0.12$) and borderline for DMS correct responses ($p=0.05$). However, paired t tests conducted on baseline vs. chronic (after repeated sessions at weeks 2-5) showed that all improvements were significant for PVT reaction time ($p<0.001$), PVT lapses ($p<0.001$), and DMS correct responses ($p<0.005$).

Figure 7:
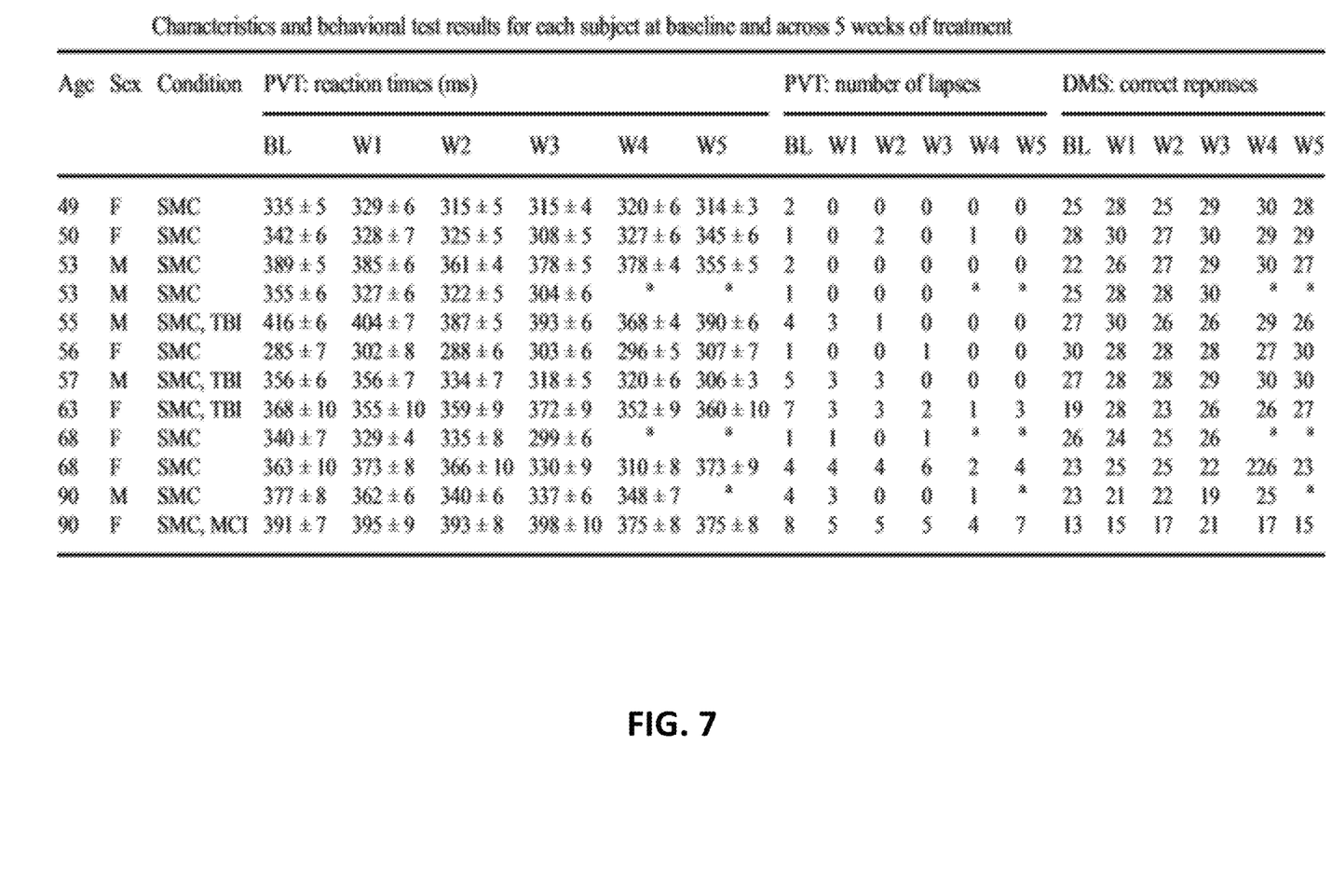
FIG. 7 is a table for characteristics and behavioral test results for each subject at baseline and across 5 weeks of treatment in the present invention.

Detailed inspection of FIG. 7 also indicated that the three participants with TBI and the one diagnosed with MCI had poorer baseline scores, with longer reaction times (mean of 383 ms compared to 348 ms in the other subjects) and larger number of lapses (mean of 6 compared to 2 in the others) in the vigilance task. However, each one of these TBI and MCI participants benefited from TILS. FIG. 7 shows improvement in all the cognitive measures of speed and accuracy for all the participants, even in the oldest most cognitively impaired participant. Specifically, the 90-year-old MCI participant reduced its reaction time from 391 ms at baseline to 375 ms during the last 2 weeks of treatment (a shorter reaction time means an improved speed of responding); the MCI participant also reduced the number of lapses in the PVT task from 8 at baseline to an average of 5.2 during the 5 weeks of treatment (a −35% reduction in the number of lapses means an improvement in vigilance); the MCI participant increased the number of correct responses in the DMS task from 13 at baseline to an average of 17 during the 5 weeks of treatment (a+31% greater number of correct responses means an improvement in working memory).

II. Increasing Carotid IMT was Related to Increasing Age and Cognitive Decline The three participants with TBI were excluded from the IMT evaluation because their brain injuries could account for their cognitive decline. The mean IMT of the rest of the sample was 0.74 mm, and values ranged from 0.55 in the youngest participant (age 49) to 1.04 in the oldest participant (age 90), increasing as a linear function of the age of the participants. Therefore, IMT and age were highly correlated ($r=0.83$) as measured by Pearson product-moment correlation statistical analysis. As expected, IMT was also related to cognitive performance. Specifically, IMT values were positively correlated with reaction time ($r=0.42$) and number of response lapses ($r=0.47$), whereas IMT values were negatively correlated with number of correct DMS responses ($r=-0.31$). Therefore, older participants with larger IMT values seemed to benefit relatively more from the TILS treatments. For example, the number of trials in which these older subjects failed to respond within 500 ms of the stimuli was reduced by 55% after a single laser treatment and by 74% after four additional laser treatments.

III. TILS Increased Resting-State EEG Alpha, Beta, and Gamma Power

Figure 8:
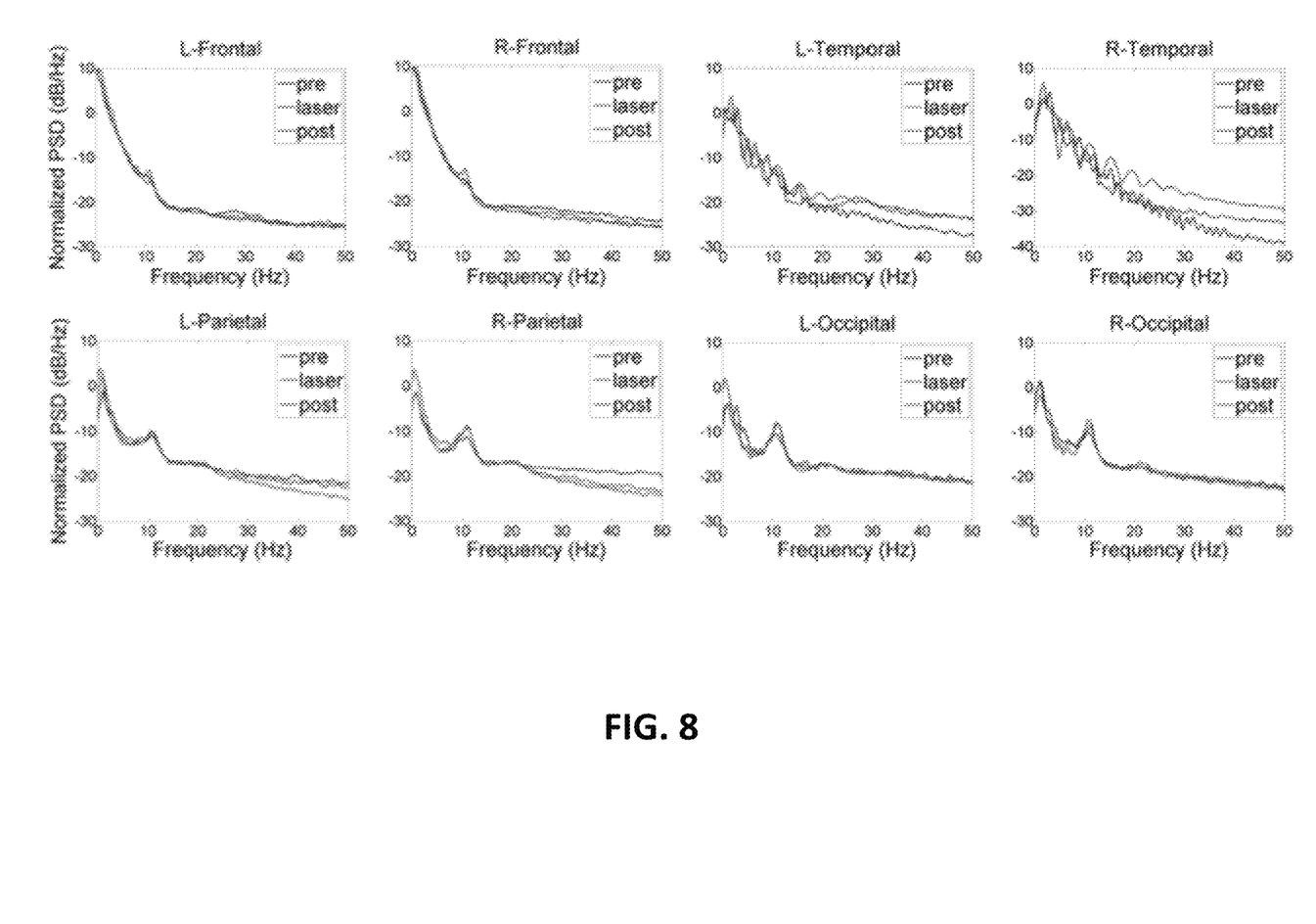
FIG. 8 shows effects of TILS on EEG power spectral density (PSD) normalized by the power within the bandwidth of 0 to 50 Hz before (pre, blue curve), during (laser, green), and after (post, red) stimulation in the present invention. TheintegralofPSD in each bandwidth is the relative power of the signal within that bandwidth. This power times epoch duration time gives the energy of the signal within that bandwidth (10 epochs of 1 min each for pre, laser, and post recording periods).
Figure 9A:
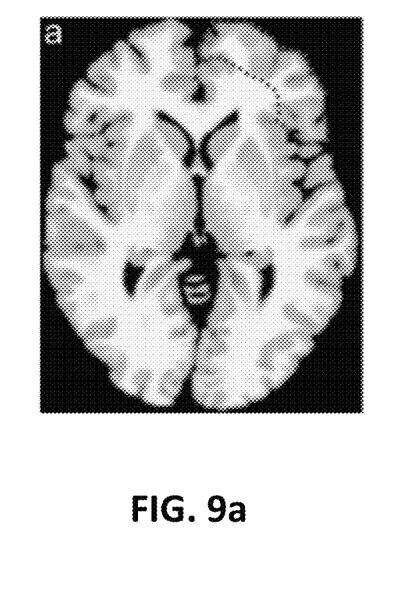
FIG. 9a is a right prefrontal cortex region with lower BOLD-fMRI responses to a two-back vs. zero-back cognitive task compared between pretreatment and post-treatment with TILS to the right forehead.
Figure 9B:
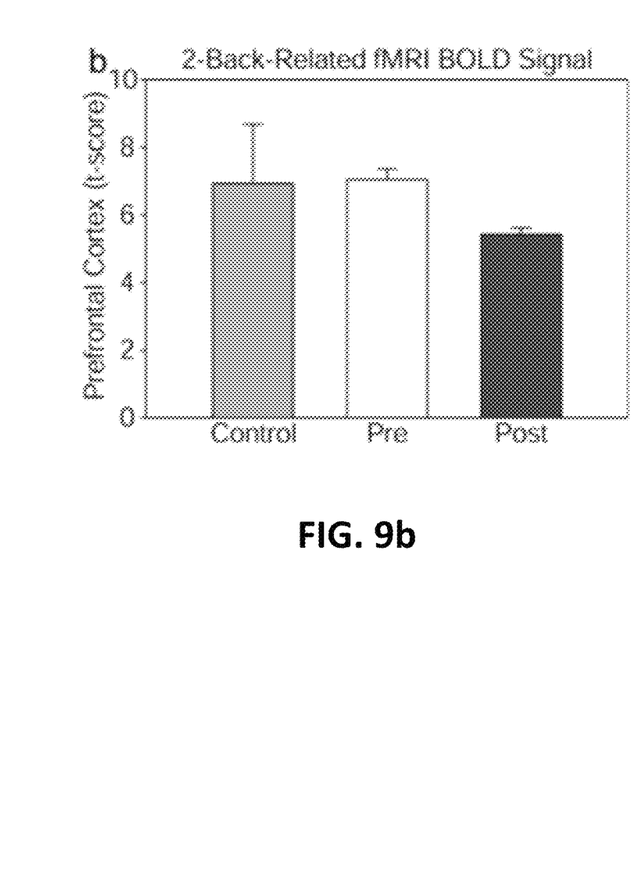
FIG. 9b illustrate bar graphs showing the corresponding values of brain intensity signal (t score) from this region, averaged between three treated subjects (pre-treatment and post-treatment) and three untreated subjects (control).

TILS effects on resting-state EEG frequencies occurred in both right and left hemispheres. FIG. 4 shows the EEG PSD normalized by the power within the bandwidth of 0 to 50 Hz. The integral of PSD in each bandwidth is the relative power of the signal within that bandwidth. There were clear enhancements of alpha power, both during and after TILS. As illustrated in FIG. 8, the largest peaks were seen in the occipital recordings, visible as peaks around 10 Hz for alpha. Similar but smaller effects were seen in the parietal recordings. Small effects were found in the frontal recordings, and no alpha effects were found in the temporal recordings. Instead, temporal recordings showed enhanced gamma power (32+Hz) and smaller increases during the laser treatment around 20 Hz for beta bands.

IV. TILS Reduced Task-Evoked BOLD-fMRI Responses

Table 3 lists the regions of interest analyzed and the corresponding stereotaxic coordinates and t scores from the mean BOLD differences between zero-back vs. two-back cognitive tasks for each region and condition. The right prefrontal cortex region which showed a BOLD decrease is delineated in FIG. 9a, with mean change in brain intensity signal from this region in FIG. 9b. Cognitive improvement was accompanied by a decrease in BOLD-fMRI signal in right prefrontal cortex areas targeted by TILS, likely indicating an improved cognitive efficiency, though the difference was only a strong trend, likely due to low number of subjects. Comparing t scores from the right prefrontal cortex (superior, middle, and inferior frontal gyri) for pre-TILS vs. post-TILS with uncorrected two tailed paired t tests gave $p<0.03$ for each comparison; the same comparisons of pre-TILS vs. controls matched by age, sex, and IMT gave $p>0.3$. The results shown in FIGS. 3 and 5 to 9 are cited from Lases Med Sci. 2017 July; 32(5): 1153-1162. doi: 10.1007/s10103-017-2221-y.

Having described the invention by the description and illustrations above, it should be understood that these are exemplary of the invention and are not to be considered as limiting. Accordingly, the invention is not to be considered as limited by the foregoing description, but includes any equivalent.

What is claimed is:

1. A system for in vivo and transcranial stimulation of brain tissue of a subject comprising at least one light source, a controller to control operation of the light source, a signal detecting unit and a processor configured to receive a signal from the signal detecting unit, analyze the signal and generate a feedback signal to the controller to control the light source until optimal results are obtained, wherein the detected signal is processed through Fourier Transform (FT) with at least one predetermined time window, which is divided by a value of the detected signal transformed by FT and integrated for a predetermined bandwidth to generate a normalized FT signals to compare with one existing signals saved in a memory unit in the processor to determine and generate the feedback signal, wherein the processor is configured to extract feature points to feed into at least one machine learning algorithms to learn and identify brain status, and the feature points include, but no limited to peaks and valleys of the normalized FT signals, including the frequencies, amplitudes, bandwidth of the integration for normalization, the integration values, the time window to get the FT and the duration of the normalized FT spectrum.

2. The system for in vivo and transcranial stimulation of brain tissue of a subject of claim 1, wherein the light source is a laser instrument.

3. The system for in vivo and transcranial stimulation of brain tissue of a subject of claim 2, wherein a wavelength of the laser instrument is 800 to 1100 nm.

4. The system for in vivo and transcranial stimulation of brain tissue of a subject of claim 2, wherein an irradiance of the laser instrument is 50 to 1000 mW/cm$^2$.

5. The system for in vivo and transcranial stimulation of brain tissue of a subject of claim 1, wherein the detecting unit is configured to detect the subject's electroencephalography (EEG) signals, functional magnetic resonance imaging (fMRI) images, blood-oxygen-level-dependent (BOLD) data.

* * * * *